United States Patent [19]

Bhattacharyya

[11] 4,151,043

[45] Apr. 24, 1979

[54] ENZYME DETERMINATION METHOD

[75] Inventor: Rabindra N. Bhattacharyya, Crestwood, Mo.

[73] Assignee: Sigma Chemical Company, St. Louis, Mo.

[21] Appl. No.: 743,350

[22] Filed: Nov. 19, 1976

[51] Int. Cl.$^2$ .............................................. G01N 31/14
[52] U.S. Cl. ....................... 195/103.5 R; 195/103.5 C
[58] Field of Search .................. 195/103.5 R, 103.5 C

[56] References Cited

PUBLICATIONS

Sibley et al., J. Biol. Chem., 177, pp. 859–872 (1949).
Dounce et al., J. Biol. Chem., 185, pp. 769–780 (1950).
Riddle et al., J. Biol. Chem., 243, pp. 2718–2724 (1968).

*Primary Examiner*—David M. Naff
*Attorney, Agent, or Firm*—Polster, Polster and Lucchesi

[57] ABSTRACT

An improved colorimetric aldolase method in which the quantity of aldolase in a sample is determined by the rate at which it enzymatically cleaves fructose-1, 6-diphosphate (FDP) into glyceraldehyde-3-phosphate (GAP) and dihydroxyacetone phosphate (DHAP); the phosphate group is hydrolyzed from the GAP and DHAP; and one of the hydrolysis products is measured. The initial enzymatic reaction is carried out in a reaction mixture containing a concentrated tris-(hydroxymethyl)-aminomethane buffer, pH 7.0, and a small quantity of sodium fluoride, but without added hydrazine or other compound to prevent the enzymatic conversion of a great majority of GAP to DHAP in the reaction mixture. Hydrolysis of the reaction products and conversion to a colored reaction product is carried out by a procedure which yields intense, long-lasting, reproducible color. An improved standard includes dihydroxyacetone carried through the same procedure.

12 Claims, No Drawings

ENZYME DETERMINATION METHOD

BACKGROUND OF THE INVENTION

This invention relates to an improved method for determining aldolase, EC 4.1.2.13, in serum and other biological fluids, and to related improved methods for determining other species.

Aldolase belongs to a group of enzymes, termed lyases, which reversibly cleave substrates into two compounds without hydrolysis. Aldolase splits the hexose fructose-1, 6-disphosphate (FDP) into the triose phosphates glyceraldehyde-3-phosphate (GAP) and dihydroxyacetone phosphate (DHAP). The term "triose" as used throughout this specification and claims is limited to the two species glyceraldehyde (GA) and dihydroxyacetone (DHA). The enzyme is present in virtually all cells of the body, especially in the muscles. Circulating blood normally contains comparatively little aldolase. Serum levels of aldolase increase in conditions which involve cell destruction, and it is believed that the normal level arises from physiologic breakdown of tissue. Clinically, the measurement of aldolase is useful, for example, in cases of muscular diseases such as progressive muscular dystrophy in which serum aldolase levels rise to five or ten times the upper limit of normal, and in prostate cancer in which the elevation of serum aldolase levels is less pronounced. Aldolase is also a commercial product, and tests are required for determining aldolase levels during the isolation of the enzyme.

Four well-known approaches to determining aldolase in serum (or equivalently, in plasma), by measuring the cleavage products of FDP, have been proposed. As set out in the article on aldolase by Bruns & Bergmeyer, in Methods of Enzymatic Analysis, ed. H. S. Bergmeyer (New York 1965), p. 724, the methods are as follows:

(1) determination of the alkali labile triose phosphate formed. Meyerhoff & Lohmann, Biochem. Z. 271, 89 (1934) and 273, 73, 413 (1934).

(2) colorimetric estimation of the triose phosphate formed by the method originally described for lactate. Dounce and Beyer, J. Biol. Chem, 173, 159 (1948).

(3) measurement of activity by the spectrophotometric method of Warburg. Warburg and Christian, Biochem. Z. 314, 399 (1943).

(4) another colorimetric method in which the dinitrophenylhydrazones of the free trioses are determined. Sibley and Lehninger, J. Biol. Chemistry 177, 859 (1949).

A fifth approach, by Jagannathan et al, Biochem. J. 63, 94 (1956), adds hydrazine to the incubation mixture and measures absorbance at 240 nm.

Meyerhoff and Lohmann's early studies were made largely on aldolase obtained from muscle extract dialysates. The high blanks, variability and technical difficulties of alkali labile phosphorus determination have led not only to its being ignored as a routine method for determining aldolase in serum or other biological fluids, but also to numerous proposals for replacing it as a primary standard. No completely satisfactory primary or secondary standard has yet been devised. See Beck, J. Biol. Chem, 212, 847 (1955). Among other things, Meyerhoff and Lohmann found that the enzyme is active between pH's of about 6 and 10 (in a carbonate-bicarbonate buffer), and that it is not influenced by certain materials, such as iodoacetic acid, sodium fluoride and sodium oxalate, which are known to inhibit some other enzymes. In later work (Bull. Soc, Chimie Biol. 20, 1033) (1938)), Meyerhoff used hydrazine to fix the relative proportions of the triose phosphates GAP and DHAP in a 1:1 ratio to permit their polarimetric determination. Fixing the proportions of GAP and DHAP is necessary because certain enzymes which may be present in biological fluids selectively catalyze destruction of one of the trioses. In particular, triose-phosphate isomerase (TPI), EC 5.3.1.1, which has a wide distribution in animal tissues, catalyzes the conversion of GAP to DHAP.

The colorimetric method of Dounce and Beyer degraded DHA and GA to acetaldehyde and added p-hydroxydiphenyl to produce a color, but their procedure suffered from frequent and variable high blanks and from the inconvenience of using concentrated sulfuric acid and heat. After the publication of the Sibley and Lehninger method, these workers modified their method by reducing the concentration of FDP substrate, adding hydrazine and adding collidine buffer pH 7.2. Dounce et al, J. Biol. Chem. 185, 769 (1950).

The method of Warburg and Christian, and other similar methods using coupled enzyme systems, suffer from several disadvantages, not the least of which is their need for an expensive ultraviolet spectrophotometer.

The colorimetric method of Sibley and Lehninger, with or without minor variations, is widely used for the determination of aldolase in serum. Sibley and Lehninger carried out the incubation of sample and FDP in Tris buffer at pH 8.6 and added hydrazine to the enzymatic incubation mixture to prevent the enzymatic conversion of GAP and DHAP through the action of TPI. After an alkaline hydrolysis step, they added an acidified 2,4-dinitrophenylhydrazine reagent to the alkaline hydrolysis mixture, then added more alkali to develop a characteristic color. The colored product is presumed to be hydrazone, and will be so characterized herein.

Some later investigators, such as Dounce et al, J. Biol. Chem., 185, 769 (1950), modified the sibley and Lehninger procedure by using a collidine buffer at a pH of 7.2 for the incubation mixture, and adding iodoacetate to the enzymatic incubation mixture to reduce side reactions and to lower the absorbance readings of the blanks used in the procedure. Friedman and Lapan, J. Clin. Lab. Med. 51, 745 (1958), recommended the use of DHA as a (secondary) standard, and the reporting of aldolase values in "DHA units".

Although the methods based on Sibley and Lehninger's method are regarded as the most reliable and suitable for routine laboratory use, all of these methods suffer from a lack of sensitivity, reliability and accuracy, from high blanks, from the instability of the colored compounds measured, and from the difficulty of preparing reliable standard solutions.

SUMMARY OF THE INVENTION

One of the objects of this invention is to provide an improved aldolase procedure which is considerably more sensitive than previously known procedures, and which, therefore, gives more meaningful normal and borderline values for aldolase in serum.

Another object is to provide such a procedure which is more accurate and reproducible than previously known procedures.

Another object is to provide such a procedure which is relatively simple and requires relatively simple equipment.

Another object is to provide such a procedure in which blanks are less variable and generally lower than with the previously known procedures.

Another object is to provide such a procedure which may utilize a reliable standard.

Another object is to provide a modification of the procedure of Sibley and Lehninger which produces a stable color proportional to aldolase concentration and is therefore readily adaptable to automatic or multiple simultaneous determinations of aldolase.

Another object is to provide such a modified procedure which is applicable to determinations of other enzymes which produce triose phosphates or trioses, and to determinations of the phosphate esters of the trioses dihydroxyacetone and glyceraldehyde and of the trioses themselves in biological fluids such as human serum.

Other objects will become apparent in light of the following description.

In accordance with one aspect of this invention, generally stated, an improved aldolase procedure is provided which includes an enzymatic incubation step in which fructose-1,6-diphosphate is incubated in a reaction mixture containing a buffer, sufficient to an inhibitor to inhibit side reactions, and a sample of human serum containing an unknown quantity of aldolase, and in which the incubation mixture is free of hydrazine or other triose "fixing" compound and the major part of the glyceraldehyde-3-phosphate (GAP) formed is enzymatically converted to dihydroxyacetone phosphate (DHAP) by triosephosphate isomerase (TPI). The DHAP is then converted to a colored hydrazone. It has been found that the quantity of TPI in human serum is sufficient to carry out the conversion of GAP to DHAP essentially as fast as GAP is formed.

In accordance with another aspect of the invention, a procedure is provided which is an improvement of the method of Sibley and Lehninger, supra, and involves alkali hydrolysis of triose phosphate at a pH of from about 11 to about 12.25 in a solution containing at least a 25 millimolar concentration of an activating amino alcohol, addition of 2,4-dinitrophenylhydrazine and acid, and alkaline color development of the reaction solution to develop a color which is proportional to aldolase concentration in the sample. In the presence of the amino alcohol and the absence of hydrazine, a color is produced which is far more intense and resistant to fading than the color produced in previous methods. The method is also useful for the determination of triose phosphates and of trioses in other systems, including systems in which the triose phosphate or triose is formed by the action of an enzyme other than aldolase.

In the preferred embodiment, the enzymatic incubation mixture includes FDP, a human serum sample, an inhibiting compound to inhibit side reactions, and a color-reaction activiting amino alcohol buffer in a concentration of at least about 0.1 molar, to maintain a pH in about the 6-9 range which favors the enzymatic cleavage. The incubation mixture does not contain hydrazine or other reactant to fix the ratio of DHAP to GAP at 1:1. The inhibiting compound is preferably sodium fluoride, and the buffer is preferably tris-(hydroxymethyl)-aminomethane (Tris) at a pH of about 7. Careful control of the alkaline hydrolysis step has been found to be critical to the formation of the colored product. The conditions are not those described by Fleisher in Standard Methods of Clinical Chemistry, Vol. 3 (New York 1961) p. 14. In particular, a pH of from about 11 to about 12.25 has been found to favor rapid and intense color development. The preferred Tris buffer has been unexpectedly found to have considerable buffering capacity, both at the pH of the enzymatic reaction and at the pH of the hydrolysis mixture. It is also an activating amino alcohol in the color forming reaction. The procedure reduces side reactions. It also produces a color which is about five times as intense as the color produced with previous procedures, and is capable of far better resolution of normal and marginal levels of aldolase in serum.

The suppression of side reactions greatly reduces the coloration of the blanks.

The new procedure also simplifies the assay of multiple samples because it produces a colored end product which is much more stable than those previously formed, and also because it permits the procedure to be interrupted after the incubation step, if necessary.

The procedure also is considerably more reproducible than previously known procedures, and utilizes a more reliable standard.

Since the work of Sibley and Lehninger, hydrazine has been universally included in the reaction mixtures of (colorimetric) procedures which hydrolyze GAP and DHAP. By eliminating hydrazine, the present procedure permits conversion of at least 90% of the GAP produced in the incubation step to DHAP. This conversion is advantageous because it has been found, in accord with the work of others (e.g. Sibley and Lehninger; see also Riddle and Lorenz, J. Biol. Chem. 243, 2718 (1968)), that DHAP forms a colored reaction product in the subsequent steps of the procedure much faster than GAP; it now appears that upon hydrolysis of the trioses, GA must isomerize to DHA before it can react further. It also now has been found that DHA is converted to hydroxypyruvic aldehyde (HPA) which in turn reacts with DNPH to form the colored reaction product. The elimination of hydrazine from the reaction system thus appears to accomplish more than merely permitting the nearly complete conversion of GAP to DHAP. Hydrazine also seems to encourage the enzymatic phosphorylation of Tris, especially in the presence of alkaline phosphatase and FDP, thereby changing the concentrations of the reactants and also giving rise to interfering colored products. It likewise competes with DNPH to form triose hydrazones and destabilizes the final colored product.

In the absence of hydrazine, a color enhancing compound is needed to produce a colored product from the reaction products of the incubation reaction. Besides Tris, other amino alcohol buffers have been found to be effective, such as Tricine, TAPS, AMPD, aminoethylpropanediol, Bis-tris-propane and AMP, and to a lesser extent serine, ethanolamine, diethanolamine, and TES. Other buffers, such as Bicine, EPPS, triethanolamine, HEPES, MOPS and PIPES were found not to be effective under the color development conditions of the preferred embodiments. The term "color enhancing" is used herein to indicate a material which, in the absence of hydrazine, produces a color at least one-quarter as intense as that produced in the presence of an equimolar concentration of Tris, under the same color formation reaction conditions.

In the absence of hydrazine, side reactions must be inhibited by an inhibiting reagent to provide accurate results and reduce the color of blanks. For example, 3-phosphoglyceraldehyde dehydrogenase may reduce the amount of color-forming reaction products in the incubation mixture. Beside sodium fluoride, other known enzyme blocking agents, such as iodoacetate, iodoacetic acid, potassium fluoride and sodium arsenite are usable. The term "inhibiting compound" is used herein to designate a material which inhibits enzymatic side reactions but does not materially interfere with either aldolase activity or TPI activity.

In the preferred embodiment, the Tris buffer is used at a pH (7.0) which is normally below the range at which it possesses sufficient buffering capacity in the enzymatic incubation step, and at a pH (about 12) which has heretofore been thought to be far above the range at which it possesses any substantial buffering capacity. Therefore, a substantially higher-than-normal concentration of buffer at both steps of the method is beneficial.

The alkaline hydrolysis step has also been found to be of great importance. In the preferred embodiment, the hydrolysis of the deproteinized TCA supernatant is carried out at a temperature of 25° C. for a timed period of twenty minutes. At this temperature, the reaction is about 90% complete, and the reaction rate after twenty minutes is low enough to make precise timing of the step less critical. The amount of color formed with DNPH is great enough to provide a sensitive procedure for even normal human serum samples.

If pure DHA is treated with alkali (pH 11–12.25) in the presence of Tris, at a temperature of 25° the reaction is more than half complete and is proceeding quite slowly after about fifteen minutes; at a temperature of 37° C. the reaction is essentially complete after ninety minutes, as evidenced by the color formed with DNPH. Pure GA, treated in the same manner, reacts more slowly. The reaction at pH 11–12.25 in the presence of Tris or other activating amino alcohol is many times greater than that in the absence of an activating amino alcohol.

DESCRIPTION OF THE PREFERRED EMBODIMENT

The following examples are illustrative of the preferred methods of the present invention.

In these examples, aldolase in a serum sample catalyzes the splitting of FDP to DHAP and GAP. TPI present in serum catalyzes the almost complete conversion of GAP to DHAP. The reaction product is hydrolyzed at room temperature to the free triose. The free triose under alkaline conditions and in the presence of Tris, is converted to hydroxypyruvic aldehyde, which reacts with 2,4-dinitrophenylhydrazine in acid to form a hydrazone. On addition of alkali, a stable, intense purple color forms with an absorbance maximum at about 560 nm. The intensity of the color is proportional to triose concentration, hence to triose phosphate concentration, hence to aldolase activity.

EXAMPLE 1

Preparation of Reagents

The following reagents are prepared:

Reagent A. FDP Substrate Solution. 1.0 gm D-Fructose-1,6-Diphosphate, Trisodium salt, is dissolved in 40 ml deionized water. The solution is stable for two weeks at 0°–5° C. or several months frozen.

Reagent B. Tris/Fluoride Buffer Solution. Tris-(hydroxymethyl)-aminomethane (0.3 mol/liter, pH 7.0 at 37° C.) and sodium fluoride (0.0015 mol/liter) are dissolved in water. Chloroform may be added as a preservative. The solution is stable at room temperature.

Reagent C. Color Reagent. 2,4-Dinitrophenylhydrazine (1 gm/liter) is dissolved in dilute (about 1.3 molar) hydrochloric acid. Stored in dark at 0°–5° C.

Reagent D. Standard Solution. Dihydroxyacetone (0.20 gm/liter) is dissolved in water. The solution is stored below 0° C. and mixed thoroughly after thawing.

Reagent E. Sodium Hydroxide Solution. Anhydrous Sodium Hydroxide (48 gms/liter) is dissolved in water. The solution is accurately standardized at 1.20 N and stored in tightly closed small containers.

Reagent F. Trichloroacetic Acid Solution. TCA (approximately 100 gm/liter) is dissolved in water to form a 0.6 N solution.

EXAMPLE 2

Preparation of Calibration Curve (Determination of DHA)

Two 100 ml Erlenmeyer flasks are labeled STANDARD and BLANK. To the STANDARD flask is added 0.4 ml calibration solution (Reagent D) and to the BLANK flask is added 0.4 ml water. To both flasks are added 4.8 ml Tris/Fluoride Buffer Solution (Reagent B), 0.6 ml substrate solution (Reagent A), and 7.7 ml water. Both flasks are placed in a 25° C. water bath for about 5 minutes to reach temperature. To each flask is added 4.5 ml sodium hydroxide solution (Reagent E), and after gentle mixing, the solutions are allowed to stand at 25° C. for exactly twenty minutes. To each is then added 6.0 ml color reagent (Reagent C.), the solutions are again mixed gently, and the flasks are placed in a 37° C. water bath. After thirty minutes, the flasks are removed from the water bath and to each is added 24 ml sodium hydroxide solution (Reagent E). The reaction mixtures are mixed by swirling. The resulting STANDARD solution color is stable for about thirty minutes, after which it fades about 2% per hour. The color of the STANDARD solution is measured against the BLANK solution at 560 ± 10 nm. If desired, a calibration curve may be prepared plotting known dilutions of the final STANDARD solution (using the BLANK solution as diluent) against absorbance.

EXAMPLE 3

Determination of Aldolase in Serum

Blood is drawn into a plain tube and allowed to clot. Serum is separated within one hour and promptly assayed or stored frozen. Hemolyzed samples are avoided.

Into two test tubes, labeled TEST and BLANK are pipetted 1.6 ml Tris-Fluoride Buffer Solution (Reagent B) and 0.2 ml serum. Both tubes are placed in a 37° C. water bath for about five minutes to reach temperature. To the tube labeled TEST is added 0.2 ml substrate solution (Reagent A). The tube is gently swirled and replaced in the water bath. After exactly thirty minutes, 2.0 ml Trichloroacetic Acid (Reagent F) is added to each tube. To the tube labeled BLANK is then added 0.2 ml substrate solution (Reagent A), and the tubes are shaken well. Both tubes are centrifuged to obtain clear supernatant, 2.0 ml of which is removed from each tube to a corresponding tube labeled TEST and BLANK. Both tubes are placed in a water bath at 25° C. for about five minutes to reach bath temperature. To each tube is then added 1.0 ml of sodium hydroxide solution (Reagent E), and after gentle mixing the tubes are allowed to stand in the 25° C. water bath for exactly twenty minutes. To each tube is added 1.0 ml color reagent (Reagent C). After gentle mixing the tubes are placed in the 37° C. water bath for thirty minutes. The tubes are removed from the bath and to each is added 4.0 ml sodium hydroxide solution (Reagent D). After mixing by inversion, the tubes are allowed to stand at room temperature for about five minutes. The contents are transferred to cuvets, and the absorbance of the TEST solution is read against the BLANK as reference, using the same instrument at the same wavelength as in the preceding example. The reading should be completed within thirty minutes after the final addition of sodium hydroxide solution.

Aldolase activity in the serum sample is determined from the calibration curve of the previous experiment. An absorbance reading equal to the absorbance of the undiluted reference indicates the splitting of 20 nanomoles (millimicromoles) of FDP per minute under the cnditions of this Example. If the splitting of one nanomole of FDP under the conditions of this Example is taken as one "unit", normal serum contains about 2 to 8 units per ml. Because the absorbance in a typical colorimeter changes more than 0.030 per unit of activity, the normal range and the borderline between normal and elevated values are easily determined.

Reproducibility studies on three serum pools assayed on ten separate occasions over a period of three weeks showed mean aldolase activities of 3.2, 6.0 and 43.8 units per ml respectively. Standard deviations were 0.06, 0.21 and 0.60, respectively. A series of fourteen sera assayed by the foregoing procedure and in terms of alkali-labile phosphate yielded aldolase values ranging from 2 to 50 units per ml and a correlation coefficient of 0.998.

If desired, the centrifuged TCA supernatants of this Example 3 may be stored frozen until the remainder of the procedure is carried out. The TEST supernatant contains both DHAP and a small amount (less than 5% of total triose) of GAP. When assayed, the thawed supernatants yield aldolase activities identical with freshly assayed samples.

Numerous variations in the methods of the present invention, within the scope of the following claims, will occur to those skilled in the art in light of this disclosure.

I claim:

1. A method for determining the concentration in a sample of biological fluid of an enzyme which catalyzes the formation of at least one triose or triose phosphate, characterized by alkaline treatment of the triose phosphate formed at a pH of from about 11 to about 12.25 in a mixture containing a color enhancing amino alcohol in a concentration of at least about 25 millimolar, said mixture being free of added hydrazine during all stages of the method, and thereafter adding a 2,4-dinitrophenylhydrazine reagent to form a colored product and relating the depth of color formed to the amount of enzyme in the sample.

2. The method of claim 1 wherein said enzyme catalyzes the formation of glyceraldehyde-3-phosphate.

3. The method of claim 2 wherein a major part of said glyceraldehyde-3-phosphate is converted to dihydroxyacetone phosphate before said alkaline treatment.

4. The method of claim 3 wherein said enzyme is aldolase.

5. The method of claim 4 wherein said sample is human serum and wherein conversion of glyceraldehyde-3-phosphate to dihydroxyacetone phosphate is accomplished by triose phosphate isomerase in said sample.

6. The method of claim 1 wherein said sample is human serum.

7. The method of claim 1 wherein said amino alcohol is tris-(hydroxymethyl)-aminomethane.

8. A method for determining the concentration of a triose phosphate in a sample of biological fluid, said method being characterized by alkaline hydrolysis of said triose phosphate at a pH of from about 11 to about 12.25 in a mixture containing a color-enhancing amino alcohol in a concentration of at least about 25 millimolar, said mixture being free of added hydrazine during all stages of the method, and thereafter adding a color-forming 2,4-dinitrophenylhydrazine reagent and relating the depth of color formed to the amount of triose phosphate in said sample.

9. The method of claim 8 wherein said sample is an unpurified biological sample.

10. A method for determining the concentration of a triose in a sample, said method being characterized by treatment of said triose at a pH of from about 11 to about 12.25 in a mixture containing a color-enhancing amino alcohol in a concentration of at least about 25 millimolar, said mixture being free of added hydrazine during all stages of the method, and thereafter adding a color-forming 2,4-dinitrophenylhydrazine reagent and relating the depth of color formed to the amount of triose in said sample.

11. The method of claim 10 wherein said sample is an unpurified biological sample.

12. A method for determining aldolase in a sample of human-serum said method comprising: incubating said sample in an incubation mixture containing fructuose-1,6-diphosphate, an inhibiting compound which inhibits enzymatic side reactions but does not materially interfere with either aldolase activity or triose phosphate isomerase activity, and a buffer, said incubation mixture containing no added hydrazine, to produce glyceraldehyde-3-phosphate and dihydroxyacetone phosphate; converting a major part of the glyceraldehyde-3-phosphate formed to dihydroxyacetone phosphate by means of triose phosphate isomerase present in said sample, thereafter hydrolyzing said dihydroxyacetone phosphate to dihydroxyacetone at a pH of from about 11 to 12.25 in a mixture free of added hydrazine during all stages of the method, and thereafter adding a 2,4-dinitro-phenylhydrazine reagent to form a colored product from said dihydroxyacetone in the presence of a color-enhancing amino alcohol in a concentration of at least 25 millimolar, said color-enhancing amino alcohol being chosen from the group consisting of Tris (tris-(hydroxymethyl)-aminomethane), Tricine (N-tris(hydroxymethyl)-methyl glycine, N-(2-hydroxy-1,1-bis(hydroxymethyl)-ethyl)-glycine), TAPS (tris(hydroxymethyl)methyl-aminopropane sulfonic acid, (2-Hydroxy-1,1-bis(hydroxymethyl)ethyl) amino)-1-propane sulfonic acid); AMPD (2-amino-2-methyl-1,3-propanol), aminoethylpropanediol, Bis-tris-propane (1,3-bis(tris(hydroxymethyl)-methylamino)-propane), AMP (2-amino-2-methyl-1-propanol), serine, ethanolamine, diethanolamine, and TES (N-tris(hydroxymethyl)methyl-2-aminoethane sulfonic acid, 2-((2-hydroxy-1,1-bis(hydroxymethyl)ethyl)amino)ethane sulfonic acid), and relating the depth of color formed to the amount of aldolase in the sample.

* * * * *